(12) United States Patent
Shaw et al.

(10) Patent No.: US 6,689,053 B1
(45) Date of Patent: Feb. 10, 2004

(54) IMA SURGICAL RETRACTOR SYSTEM

(75) Inventors: David P. Shaw, Christchurch (NZ); John T. M. Wright, Denver, CO (US)

(73) Assignee: Genesee Biomedical, Inc., Denver, CO (US)

( * ) Notice: Subject to any disclaimer, the term of this patent is extended or adjusted under 35 U.S.C. 154(b) by 99 days.

(21) Appl. No.: 09/975,788

(22) Filed: Oct. 11, 2001

(51) Int. Cl.$^7$ ............................................... A61B 17/00
(52) U.S. Cl. ........................ 600/227; 600/228; 600/231
(58) Field of Search ................................ 600/201, 215, 600/227, 228, 229, 230, 231, 233

(56) References Cited

U.S. PATENT DOCUMENTS

| | | | |
|---|---|---|---|
| 3,046,072 A | * | 7/1962 | Douglass, Jr. et al. |
| 3,749,088 A | * | 7/1973 | Kohlmann .................. 600/234 |
| 4,622,955 A | | 11/1986 | Fakhrai |
| 5,065,739 A | | 11/1991 | Forrest et al. |
| 5,109,831 A | | 5/1992 | Forrest et al. |
| 5,474,056 A | | 12/1995 | Laborie et al. ............. 600/214 |
| 5,667,481 A | * | 9/1997 | Villalta et al. .............. 600/231 |
| 5,938,592 A | * | 8/1999 | Koteles et al. ............. 600/227 |
| 5,964,699 A | | 10/1999 | Rullo et al. ................. 600/228 |
| 5,984,866 A | | 11/1999 | Rullo et al. ................. 600/231 |
| 6,017,306 A | * | 1/2000 | Bigliani et al. ............. 600/234 |
| 6,083,153 A | | 7/2000 | Rullo et al. ................. 600/217 |
| 6,090,042 A | | 7/2000 | Rullo et al. ................. 600/210 |
| 6,228,026 B1 | | 5/2001 | Rullo et al. ................. 600/227 |
| 6,241,659 B1 | * | 6/2001 | Bookwalter et al. ........ 600/231 |

OTHER PUBLICATIONS

Kobina IMA Retractor description downloaded from Geister Medizintechnik GmbH website (www.geister.com/produkt_022_eng.html) on Sep. 10, 2001.
Omni–Tract Surgical IMA Retractor description downloaded from Omni–Tract website (www.omni–tract.com/cs200.htm) on Sep. 10, 2001.

* cited by examiner

*Primary Examiner*—Cary E. O'Connor

(57) ABSTRACT

A retractor system that is easily and quickly attached to the operating room table utilizing low profile retractor blades which minimize obstruction of the surgeons view and access to the surgical field. Retraction is accomplished quickly and simply with virtually infinite variability using a single or dual generally linear ratcheting system that gently and controllably elevates one side of an incision and moves it away from the other side of the incision.

16 Claims, 3 Drawing Sheets

IMA SURGICAL RETRACTOR SYSTEM

CROSS-REFERENCE TO RELATED APPLICATION

This invention relates to surgical appliances and, more particularly, to systems for retracting the sternum for gaining access for cardiovascular surgery, principally coronary artery bypass grafting using the internal mammary artery.

1. Background of the Invention

Coronary artery bypass grafting (CABG) in humans was introduced nearly a half century ago. The first reported CABG using the internal mammary artery (IMA) in humans was performed in 1960. However, saphenous vein grafting became the most common CABG technique for the next two decades. By the mid 1980's, however, it was recognized that the long-term survival rate of CABG was significantly higher when the IMA rather than the saphenous vein was used. Saphenous vein grafting supplemented by the IMA and occasionally gastroepiploic artery, inferior epigastric artery, and radial artery, has enabled complete arterial revascularization to be performed in almost all patients. Coronary artery bypass grafting is the most common procedure performed in adult cardiovascular surgery today. In the graft selection for CABG, the first choice is the left IMA and the second choice is the right IMA.

The IMA is in close proximity to the heart and therefore it is not necessary to completely remove it from the patient. The side branches are hemostatically severed, the main trunk of the vessel is occluded with a clamp, and then the IMA is severed at a point just superior to the patient's diaphragm so that the IMA is mobilized without disconnecting it from its original blood supply. The freed end of the IMA is then anastomosed to a coronary artery, usually to the left anterior descending coronary artery, just distal to the stenosis.

The procedure for harvesting the IMA requires significant access and visibility into the underside of the upper thoracic cavity for the surgeon. The surgeon must free the IMA from the wall of the internal thoracic cavity. The side branches of the IMA must be located and transected with minimal blood loss.

The most commonly used method of access to the thoracic cavity for the mobilization of the IMA and the anastomosis of it to the left anterior descending coronary artery is a median sternotomy. For this procedure, a longitudinal incision is made through the patient's sternum on the midline of the chest. Then a surgical retractor is used to spread and hold apart the left and right rib cages, creating an opening. Since the IMA is attached to the thoracic cavity wall, the angle of approach the surgeon must use through the opening is very difficult since the inferior rib cage tends to obstruct the manipulation of surgical devices used for the procedure.

It is also important that the retracting apparatus be easy to clean and sterilize for reuse, or that it be low cost and disposable. The retractor must be stable during the surgical procedure, to maintain the lifting/retracting orientation desired by the surgeon, and to be as atraumatic as practical to the surgical patient. It is also highly desirable that the retractor allow for only the amount of retraction required by the surgeon to further minimize patient trauma.

2. Discussion of the Prior Art

Fakhrai, U.S. Pat. No. 4,622,955, describes a surgical retractor to be mainly used for dissection of the internal mammary artery. It is fixed to the side of the operating bed by a clamp which can be moved over the rail for the desired place. It's pole will be at either side that internal mammary artery is intended to be dissected, side arm of the pole will be over the patient and holding the crank mechanism to which retractor hooks are attached by a cable. By placing the hooks of the retractor at the edge of the sternum, after being split at the middle, and cranking the handle the sternum is retracted. The crank portion of the retractor, which is adjustable over the side arm of the pole, will pull and elevate the side of the chest and hold it in position for the time that is needed for the dissection of the internal mammary artery.

Other crank operated retractors are described by Rullo, et. al., in U.S. Pat. Nos. 5,964,699; 5,984,866; 6,083,153; 6,090,042; and 6,228,026. Rullo, et al., U.S. Pat. 6,083,153, describes, for example, a xiphoid retraction system that includes a set of rakes for use as surgical retractors in a surgical procedure in which the set of rakes includes a progressively longer body-supporting base portion and a C-shape surgical retraction device adapted for use in a mid-cab surgical procedure. A set of rib rakes are provided for retraction of the patient's ribs and thoracic region in a mid-cab procedure, in which each retractor rake has a progressively larger body-supporting portion for use in, for example, the dissection of the internal mammary artery during its harvest for use in a coronary bypass procedure.

A similar concept, for use in breast implant surgery and using a pulley, is described by Forrest, et. al., in U.S. Pat. Nos. 5,065,739 and 5,109,831.

The method of using retraction apparatus depends, of course, on the particular surgical procedure with which it is used and the preference of the surgeon rather than upon the particular apparatus per se. In a general sense, however, a common method has been used for many years and is described here simply as an example of methods that can be used. An incision is made in a patient extending from near the patient's xiphoid process to near the patient's manubrium and a retractor device of some sort is attached to the patient's sternum, typically with one blade or rake near an attachment point of the patient's xiphoid process and a second blade near the manubrium. A retracting force is applied to the retractor to enlarge the surgical cavity.

While prior art apparatus using crank devices or pulleys perform the necessary retracting function, they are quite complex mechanically, difficult to assemble and use, and prone to malfunction during surgery. One common problem with the prior art devices is use of a single retractable cable attached to a horizontal support which secures the retractor rakes. This structure causes pivoting of the horizontal support about the point of cable attachment and makes independent actuation of the retractor rakes to provide precise amounts of retraction difficult or impossible. The advantages of prior art crank retractor systems is retained in the present invention but the present device is much easier to assemble and to use and is more reliable in use. In addition, more stable, precise retraction is obtained because the degree and direction of retraction is not dependent upon cables or chains which tend swing about. Moreover, the present invention enables independent actuation of retractor blades or rakes, which facilitates minimal patient trauma.

Geister Medizintechnik GmbH produces the "Kobinia IMA" retractor that uses an axially rotated knob which engages a coarse screw thread on a retractor shaft to actuate the retractor. The Omni-Tract Surgical "Pittman IMA" has a similar design. Rotating the knob is slow and cumbersome and provides minimal mechanical advantages to the user. The threads of the retractor shaft also provide a crevase that complicates cleaning and sterilization.

The retractor system described herein provides the advantages described and solves some of the above problems. A surgical access of variable size is provided using an easily adjustable but very stable set of mechanisms. The retractor is easily sterilized such that it can be reused with complete safety. The retracting mechanism is largely out of the surgical field and thus provides maximum access to the surgical sites.

SUMMARY OF THE INVENTION

A first aspect of the present invention is a surgical retractor system for retracting tissue of a patient. The retractor system includes a horizontal support and first and second retractors are attached to the support. The first and second retractors are laterally spaced along the support to enable independent retraction of a patient's tissue at select points spaced lengthwise of the patient. A gimbaled attachment is provided between at least one of the first and second retractors facilitating and the horizontal support. The gimbaled attachment preferably facilitates lengthwise movement of the retractor along the horizontal support. Preferably the horizontal support consists of a bar having a diameter and a gimbaled attachment consists of a support passage axially receiving the bar defined in the retractor. The support passage includes a curved surface configured to engage the bar diameter tangentially to provide selective lengthwise and gimbaled movement of the retractor relative to the horizontal support. The support passage preferably includes a major dimension substantially perpendicular to the support bar and a minor dimension perpendicular to the major dimension. The minor dimension is slightly longer than the diameter of the bar and the curved surface extends into the minor dimension to provide an effective diameter of the minor dimension that is less than the diameter of the bar.

The retractor preferably includes a retractor shaft having a distal and a proximal end with a tissue engaging blade on the distal end. A ratchet receives the retractor shaft between the distal and proximal ends to enable selective retraction of the patient's tissue engaged by the blade along a first direction. The ratchet preferably includes a frame and a release trigger defining a first hole receiving the retractor shaft. The release trigger is pivotally attached to the frame and biased to engage the perimeter of the first hole with the retractor shaft to prevent movement of the retractor shaft relative to the frame in a second direction opposite the first direction. The ratchet may further include an actuator defining a second hole receiving the retractor shaft spaced lengthwise of the retractor shaft from the release trigger. The actuator is operatively associated with the frame to engage the perimeter of the second hole with the retractor shaft upon movement of the actuator in an actuation direction relative to the frame to move the retractor shaft in the first direction. The actuator preferably consists of an actuator plate defined the second hole and an actuator handle pivotally attached to the frame and operatively associated with the actuator plate to engage the perimeter of the second hole with the shaft upon pivoting of the actuator handle in the actuation direction.

A second aspect of the present invention is a surgical retractor consisting of a retractor shaft having a distal and proximal end with a tissue engaging blade on the distal end and a ratchet which receives the retractor shaft between the distal and proximal ends to enable selective retraction of patient tissue engaged by the blade along the first direction. The ratchet preferably includes a gimbaled attachment to the support member. The support member is preferably a bar having a diameter and the gimbaled attachment includes a support passage defined in the ratchet for axially receiving the bar. The support passage includes a curved surface configured to engage the bar diameter tangentially to provide selective gimbaled movement of the ratchet relative to the bar. The ratchet preferably consists of a frame and a release trigger defining a first hole receiving the retractor shaft. The release trigger is pivotally attached to the frame and biased to engage the perimeter of the first hole with the retractor shaft to prevent the retractor shaft from moving relative to the frame in a direction opposite the first direction. An actuator defining a second hole receiving the retractor shaft is preferably operatively associated with the frame to engage the perimeter of the second hole with the retractor upon movement of the retractor in an actuation direction relative to the frame to move the retractor shaft in the first direction. The retractor may consist of an actuator plate defining the second hole and an actuator handle pivotally attached to the frame and operatively associated with the actuator plate to engage the perimeter of the second hole with the shaft upon pivoting of the actuator handle in the actuation direction.

The retractor system of the present invention is easy to set up and can be set up quickly. It can be attached to the operating room table and completely set up in less than a minute. The subject retractor system utilizes low profile retractor blades which minimize obstruction of the surgeons view and access to the surgical field. Retraction is accomplished quickly and simply with virtually infinite variability using a system that gently and evenly elevates the sternum. The retractor system has particular utility for IMA dissection that facilitates grafting of an internal mammary artery to an anterior descending coronary artery.

DESCRIPTION OF THE PREFERRED EMBODIMENT

The presently preferred embodiment of the invention is described in connection with the drawings which depict the preferred embodiment. However, many other embodiments can be made which incorporate the invention; thus, neither the description nor the drawings are necessarily limiting. Materials are referred to in connection with the various components of the invention; however, materials per se are not critical to the invention and other materials are presently available and it is expected that other alloys and materials will become available from which these components can be made without departing from the invention. At the present time, the components are fabricated principally of stainless steel.

The invention is described for convenience as an IMA retractor system, however, surgeons will find the retractor system useful for other surgeries as well as for use in grafting of an internal mammary artery to an anterior descending coronary artery.

Figure 1:
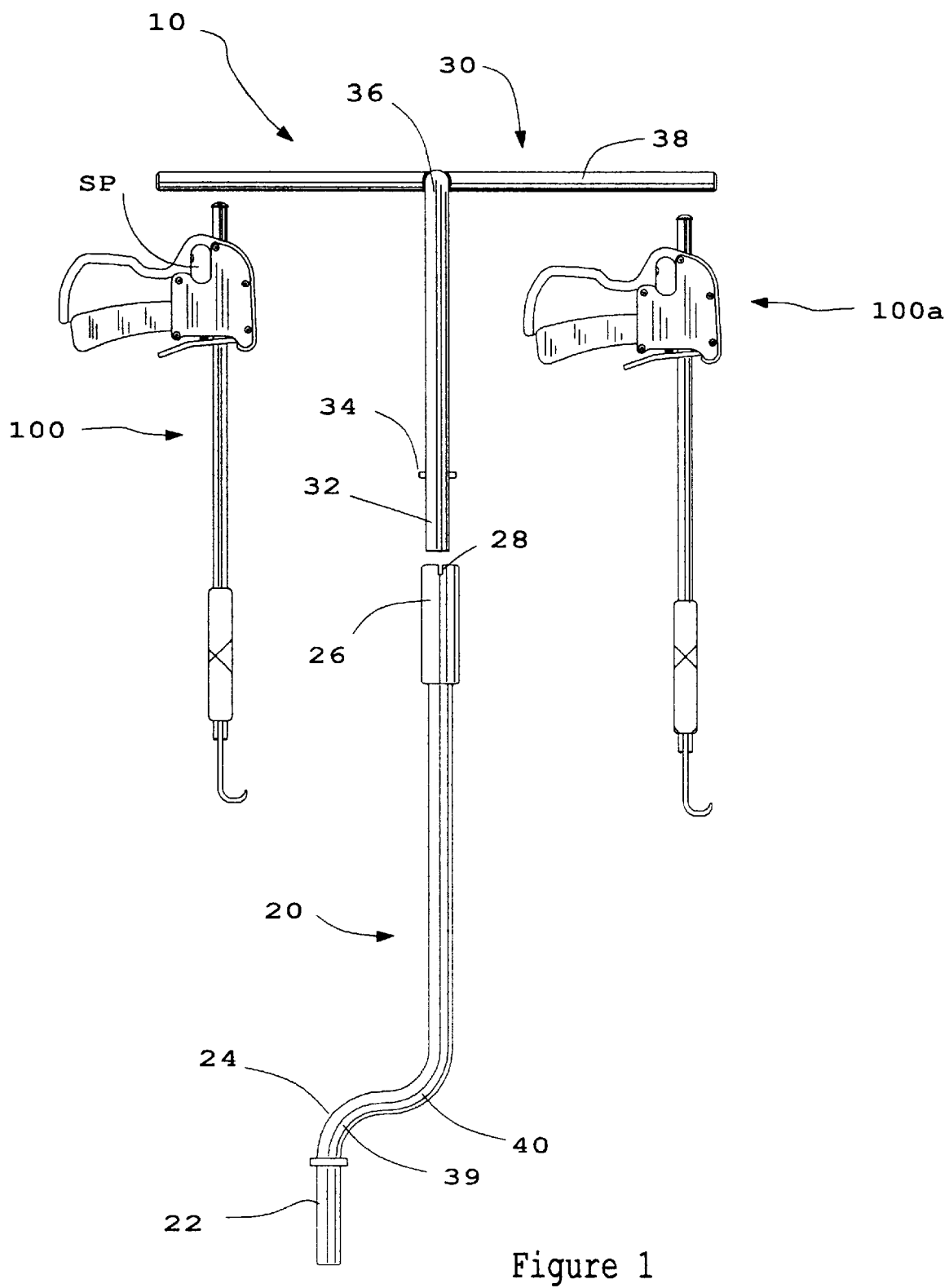
FIG. 1 is a plan view of the retractor system of this invention showing each of the components disassembled from each other but arranged to suggest the manner of assembly.

The IMA retractor system 10 comprises four or more major components which are depicted in FIG. 1. The system may comprise one, two (as shown) or more retractors, indicated at 100 and 100a.

A vertical support shaft 20 is connectable to convention operating room table brackets by means of a base shaft portion 22 on the proximal end that slips into the sleeve found in such brackets. It will be readily understood that any means for connecting the vertical support shaft 20 to the table may be used without departing in the least from the concept and scope of the invention. The vertical support shaft preferably, but not necessarily, defines a double L curved portion 24 which allows the vertical portion to extend vertically over the operating table or vertical from a distance away from the sides of the operating room table. The distal end of the vertical support shaft is so constructed as to define a socket 26 for receiving a T-bar retractor support member.

The T-bar retractor support member 30 comprise a shaft that is vertical when supported, the proximal end 32 of which is inserted into the socket 26. The pin 34 is received in the locking slot 28 formed in the distal end of the socket 28 and prevents rotation of the pin 34 in the socket 26. Of course, the locking mechanism is not essential to the operation of the system, but is very convenient, and other locking mechanisms could easily be substituted. The shaft 36 is constructed to define an L curve proximate the distal end thereof, the distal end of the shaft 36 being fixed to a cross-bar 38 from which the retractors are suspended when in use. Right angle bends 39 and 40 serve to displace upright 20 horizontally so that it will not contact the patient's arm, thus minimizing brachial nerve damage which might otherwise occur.

Figures 2, 3, 4:
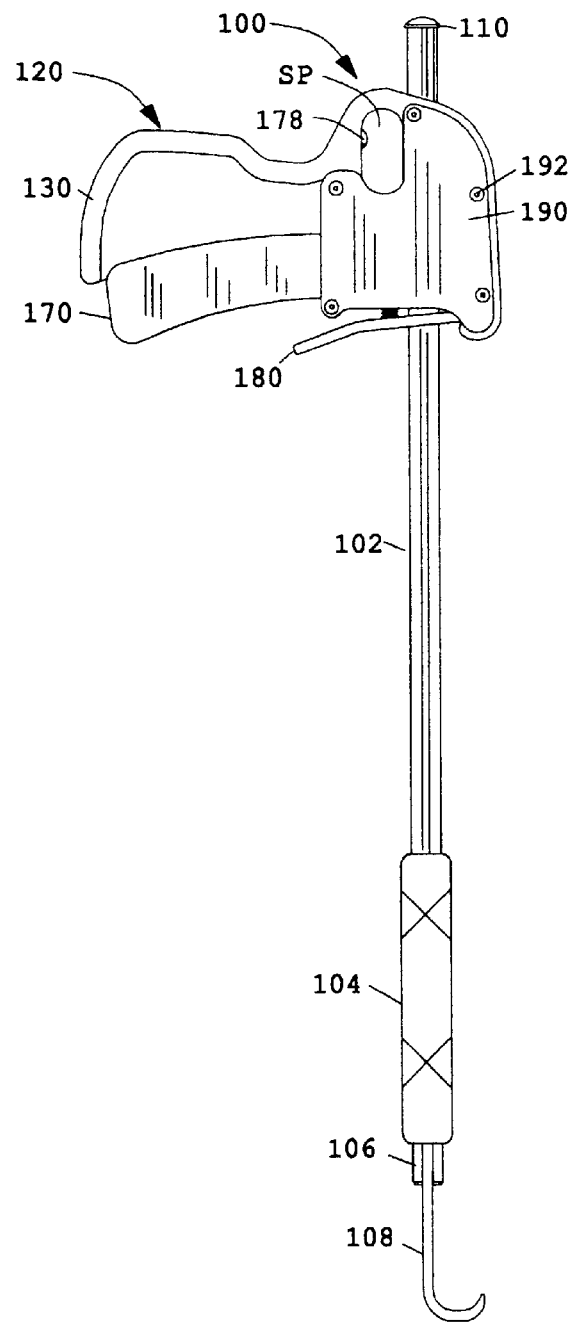
FIG. 2 is a side plan view of one of the retractors, the other retractor being identical in construction.
FIG. 3 is a side enlarged view, broken in the middle, depicting one of the retraction blade assemblies, the other retraction assembly being identical.
FIG. 4 is a front enlarged view, broken in the middle, depicting one of the retraction blade assemblies, taken at right angles to the view in FIG. 3.

The IMA retractor system normally comprises two identical retractors 100, one of which is more fully depicted in FIG. 2, to which reference is now made.

Figure 5:
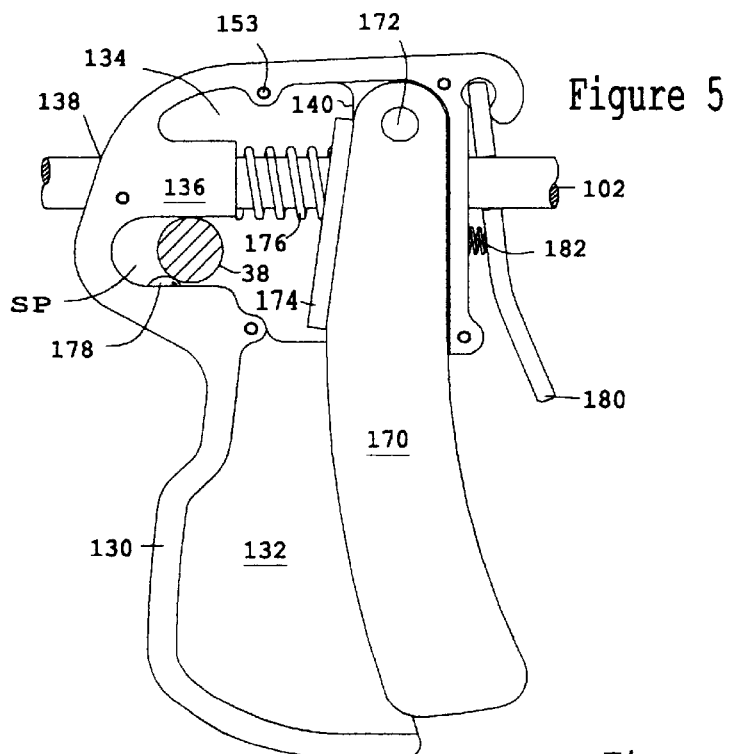
FIG. 5 is a side plan view of one of the retractor actuator ratchet mechanism shown with the cover plate removed, the other retractor actuator ratchet mechanism being identical.
Figure 6:
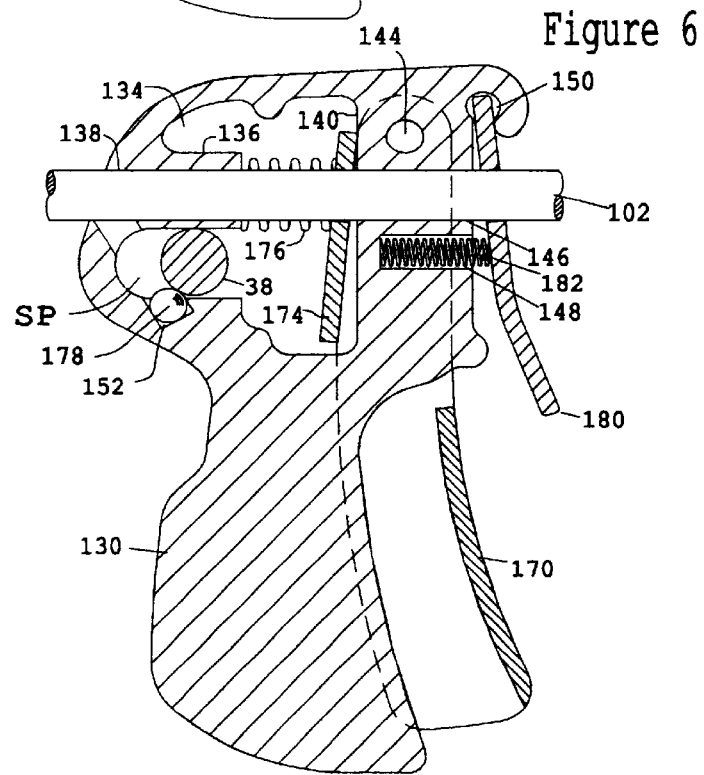
FIG. 6 is a cross-sectional view of one of the retractor actuator generally linear ratchet mechanism, the cross-section taken through the center of the mechanism.

The retractors 100 comprise a retractor shaft 102, the distal end of which are configured and constructed to define a grip 104, blade holder 106 and a retractor rake or blade 108. A keeper screw 110 which has a diameter slightly larger than the shaft is threadably received in a threaded aperture (not shown) in the proximal end of the shaft to prevent the shaft from accidentally falling out of the retractor actuating generally linear ratchet mechanism 120, to be described hereinafter. Other keepers could, of course, be used with nearly equal convenience. The shaft, grip, blade holder and blade are conveniently welded to form a unitary member that can be easily sterilized. Alternatively, they may be constructed of separate components, the grip and blade holders forming a chuck for removably receiving the proximal end of the blade. In this instance, the components would be separated for sterilization. As shown in FIG. 2 the retractor shaft 102 extends through the retractor ratchet mechanism 120, The retractor ratchet mechanism 120 is best described in connection with FIGS. 5, 6 and 7 to which reference is now made. The retractor ratchet mechanism 120 comprises a handle grip 130 which, as best shown in FIG. 5, comprises an enlarged outer flange on the grip side, the left side as shown in FIGS. 5 and 6, and a central web section 132. The retractor ratchet mechanism defines an opening there through 134 from side to side into which a sleeve body 136, formed as part of the hand grip 130, extends and through which a sleeve passage 138 is formed for slidably receiving the shaft 102, best shown in FIG. 6. The handle grip is also constructed to define a forward guide portion 140 which defines a spring receptor 148 and a guide sleeve passage 146, also for slidably receiving the shaft 102. A pivot pocket 150 is also formed by the handle grip body 130, the function of which will be apparent from the following description.

An actuator handle 170 is pivotally connected by a pin 172, extending through the aperture 144 in hand grip body 130. The lower portion, as shown in FIGS. 5 and 6, of the actuator handle 170 is formed to define a U shape, the opening of which is to the left, as shown, and which receives the web portion 132 of the hand grip 130.

The upper left portion, as shown, of the actuator handle 170 contacts an actuator plate 174 which defines a passage through which the shaft 102 passes. The shaft 102 also receives there-around an actuator plate return spring 176, the spring being in compression between the actuator plate 174 and the sleeve body 136.

The handle grip body 130 is configured and constructed to define a recess 152 for receiving a ball bearing 178 to form a fixed ball-detent, which is an important feature of the invention. The recess 152 has a diameter slightly less (typically 0.0002") than the hardened stainless steel ball, (typically made of type 440C stainless steel), which is pressed into the recess 152. Alternatively, lips may be swaged or formed to retain the ball therein. The function and advantages of this arrangement are described more fully hereinafter.

The shaft 102 also extends through a passage formed in a release trigger 180, the upper end, as shown in FIGS. 5 and 6, is pivotally received in the pivot pocket 150 formed in the hand grip body 130. A release trigger return spring 182 is received in the spring receptor cavity 148 in the grip body and is retained in compression biasing the release trigger 180 to the right, as shown, in which position the release trigger permits movement of the shaft in a retraction or first direction to the left but not to the right as depicted in FIGS. 5 and 6.

In the preferred embodiment, the actuator plate 174, the release trigger 180 and the retractor shaft 102 are all made of a hard, corrosion resistant alloy, such stainless steel 17-4 PH hardened to 44 Rc.

Figure 7:
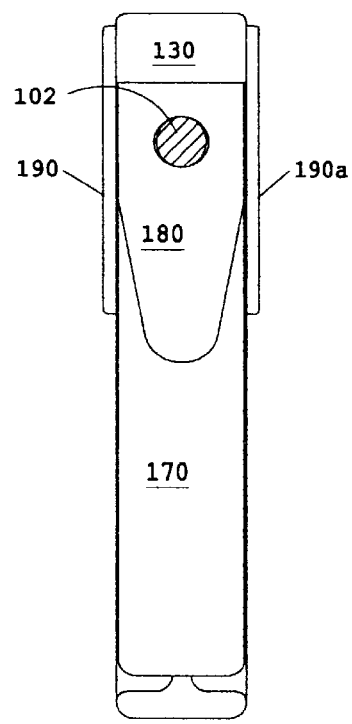
FIG. 7 is a front elevation view of one of the retractor actuator ratchet mechanisms, viewed from the direction in which the blade assembly extends.

The opening 134 from side to side of the hand grip 130 and the mechanisms therein are covered with a pair of plates 190 and 190a on the respective sides, shown in FIG. 7, the plates being retained by means of screws 192 received in conveniently located threaded apertures as shown typically at 153 in FIG. 5.

The assembly and operation of the IMA retractor system will now be described making reference to all of the figures as appropriate.

The vertical support shaft 20 is connected to extend outwardly and upwardly from the side rail of the operating room table by means of a suitable clamp which securely fixes the base shaft portion 22 on the proximal end to the side rail on the operating table. Typically, the clamp comprises means for gripping the rail of the operating table and forms a receptacle for receiving and fixing the location of the base shaft portion 22. Of course any clamp or device which performs this function may be used. The vertical support shaft extends vertically from a location spaced from the sides of the operating room table.

The T-bar retractor support member 30 is inserted into the socket 26 with the pin 34 in the locking slot 28 with the cross-bar 38 extending laterally, generally parallel and above the side of the operating room table.

The IMA retractor system normally comprises two identical retractors 100 and 100a which are suspended from and supported by the cross-bar. Since these retractors identical only one is depicted and described in detail. More than two retractors could, of course, be used but additional retractors are normally not useful and additional retractors would tend to interfere with access to the surgical field.

As best shown in FIG. 1, the retractor defines a support passage SP there through from side to side. The support passage SP is more particularly located in the ratchet mechanism 120 portion of the retractor. This support passage is non-circular having a major dimension parallel to the shaft 102 (and perpendicular to the cross-bar 38) that is greater than the minor dimension perpendicular to the shaft. The minor dimension is slightly larger, e.g., 5%, than the diameter of the cross-bar 38. The ball 178 in the ball-detent cavity extends from one of the minor dimension sides of the support passage into the support passage such that the distance from the ball to the opposite side of the passage is slightly less, e.g., 10%, than the diameter of the cross-bar 38 and, preferably is closer to the rear side (upper side in FIG. 1, left side in FIG. 5) of the support passage of the retractor actuator ratchet mechanism than to the front (lower side in FIG. 1, right side in FIG. 5) of the support passage.

The cross-bar is passed through the support passage SP below, in use and as shown in FIG. 1, of the ball-detent and is, in effect, clamped between the ball and the opposite side of the support passage. Since the support passage is longer in the major dimension than the diameter of the cross-bar and because the ball makes point contact with the cross-bar, the retractor is free to rotate in a gimbaled manner around the cross-bar 38 and to move lengthwise of the cross-bar. The retractor can be suspended at an angle other than vertical. Indeed, the retractor can be suspended relative to vertical at any angle up to about 30 degrees in any direction and, of course, greater that 30 degrees forwardly or rearwardly with respect to the vertical shaft 36.

It is noted that rotation of the ball 178 in recess 152 is not necessary because relative movement is possible between the tangential contact of the ball with the cross-bar. Thus, the operation of the system does not require that the ball rotates. The important feature of this structure of the mechanism is that the retractor is supported on the cross-bar by one side of the support passage and on the other side by a tangential, or generally tangential, contact with a hemispheric, or generally hemispheric, e.g., a solid elliptical, structure. A solid elliptical surface or the surface of a solid body having at least one curved surface which permitted a tangential contact would suffice. The curved surface is preferably added as a ball or curved-surface body made of hardened stainless steel; however, the means forming the support passage can be machined or milled to form a curved surface for engaging the cross-bar. The curved surface is preferable intermediate the ends of the support passage but can be formed in the end of the support passage that supports the retractor.

The retractors are suspended as described from the cross-bar and the retractor blades are engaged under the cut edge of the sternum adjacent the sternal incision, usually with one close to each end of the sternum (i.e. near the xiphoid process and near the manubrium). The surgeon grasps one retractor body 130 with one hand and grasps grip 104 or the corresponding retractor shaft 102 and pushes grip 104 upwards and outwards toward the ratchet mechanism 120. This is repeated with the other grip/body. These initial maneuvers take only a few seconds. The side of the sternum which the blades engage is thus lifted upwardly and outwardly very quickly. The two retractors are then actuated separately giving visual and operational access to the mammary artery and the heart, and, thus, permit gentle retraction in two areas (or more if more than two retractors are used), to the degree necessary to perform the operation with minimum trauma.

Retraction is accomplished by gripping the ratchet mechanism 120 handle grip 130 and actuator handle 170 and squeezing them together in an actuation direction. This causes the actuator plate 174, which defines a passage through which the shaft 102 passes, to grip the shaft 102 and move the shaft in the first or retraction direction (upwardly in FIG. 1) approximately 0.15" in the ratchet mechanism as shown in FIG. 1. The actuating ratchet mechanism produces a mechanical advantage or about 5:1. Thus, the sternal edge of patients with stiff chests may be elevated with ease. This squeezing action is repeated until the necessary retraction is accomplished, the actuator plate return spring 176 resetting the actuator plate after each such action, the release trigger preventing downward movement of the shaft. When the release trigger is grasped and squeezed, the shaft is released for downward movement, but cannot fall out because of the keeper screw 110 in the end of the shaft, which cannot pass through the passage 138.

Following surgery, the retractor shafts are released and removed from the patient and the IMA retractor system removed from the operating table, partially disassembled, cleaned and sterilized and stored for repeated use.

What is claimed is:

1. A surgical retractor system for retracting tissue of a patient comprising:
   a support;
   a first and a second retractor, the first and second retractors being laterally spaced along the support to enable independent retraction of a patient's tissue at select points; and
   means for gimbaled attachment between the support and at least one of the first and second retractors.

2. The surgical retractor system of claim 1 wherein the gimbaled attachment means facilitates selective movement of the retractor along the support.

3. The surgical retractor system of claim 1 wherein the support comprises a bar having a diameter and the gimbaled attachment means comprises a support passage axially receiving the bar defined in the retractor, the support passage including a curved surface configured to engage the bar diameter tangentially to provide selective lengthwise and gimbaled movement of the retractor relative to the support.

4. The surgical retractor system of claim 3 wherein the support passage comprises a major dimension substantially perpendicular to the bar and a minor dimension perpendicular to the major dimension, the minor dimension being slightly longer than the diameter of the bar and the curved surface being configured to extend into the minor dimension to provide an effective diameter of the minor dimension that is less than the diameter of the bar.

5. The surgical retractor system of claim 1 wherein at least the first retractor comprises:

a retractor shaft having a distal and a proximal end with a tissue engaging blade on the distal end; and a ratchet receiving the retractor shaft between the distal and proximal ends to enable selective retraction of the patient's tissue engaged by the blade along a first direction.

6. The surgical retractor system of claim 5 wherein the ratchet comprises:

a frame; and a release trigger defining a first hole receiving the retractor shaft, the release trigger being pivotally attached to the frame and biased to engage the perimeter of the first hole with the retractor shaft to prevent movement of the retractor shaft relative to the frame in a second direction opposite the first direction.

7. The surgical retractor system of claim 6 wherein the ratchet further comprises an actuator defining a second hole receiving the retractor shaft spaced lengthwise of the retractor shaft from the release trigger, the actuator being operatively associated with the frame to engage the perimeter of the second hole with the retractor shaft upon movement of the actuator in an actuation direction relative to the frame to move the retractor shaft in the first direction.

8. The surgical retractor system of claim 7 wherein the actuator comprises:

an actuator plate defining the second hole; and an actuator handle pivotably attached to the frame and operatively associated with the actuator plate to engage the perimeter of the second hole with the shaft upon pivoting of the actuator handle in the actuation direction.

9. The surgical retractor system of claim 1 further comprising a vertical support attached to the support for rigidly suspending the support horizontally above a patient.

10. A surgical retractor comprising:

a retractor shaft having a distal and a proximal end with a tissue engaging blade on the distal end; and a ratchet receiving the retractor shaft between the distal and proximal ends to enable selective retraction of patient tissue engaged by the blade along a first direction, with the ratchet providing a mechanical retraction advantage greater than 1:1 as retraction occurs.

11. The surgical retractor system of claim 10 wherein the ratchet comprises means for gimbaled attachment to a support member.

12. The surgical retractor system of claim 11 wherein the support member is a bar having a diameter and the attachment means comprises a support passage defined in the ratchet for axially receiving the bar, the support passage including a curved surface configured to engage the bar diameter tangentially to provide selective lengthwise and gimbaled movement of the ratchet relative to the bar.

13. The surgical retractor system of claim 12 wherein the support passage comprises a major dimension substantially perpendicular to the bar with the bar axially received in the support passage and a minor dimension perpendicular to the major dimension, the minor dimension being slightly longer than the diameter of the bar and the curved surface being configured to extend into the minor dimension to provide an effective diameter of the minor dimension that is less than the diameter of the bar.

14. The surgical retractor system of claim 10 wherein the ratchet composes:

a frame; and a release trigger defining a first hole receiving the retractor shaft, the release trigger being pivotally attached to the frame and biased to engage the perimeter of the first hole with the retractor shaft to prevent movement of the retractor shaft relative to the frame in a second direction opposite the first direction.

15. The surgical retractor system claim 14 further comprising an actuator defining a second hole receiving the retractor shaft, the actuator being operatively associated with the frame to engage the perimeter of the second hole with the retractor shaft upon movement of the actuator in an actuation direction relative to the frame to move the retractor shaft in the first direction.

16. The surgical retractor system of claim 15 wherein the actuator comprises:

an actuator plate defining the second hole; and an actuator handle pivotably attached to the frame and operatively associated with the actuator plate to engage the perimeter of the second hole with the shaft upon pivoting of the actuator handle in the actuation direction.

\* \* \* \* \*